United States Patent
Medoff

(10) Patent No.: US 8,216,238 B2
(45) Date of Patent: Jul. 10, 2012

(54) METHOD OF USING AN INTRAMEDULLARY IMPLANT FOR FRACTURE FIXATION

(75) Inventor: Robert J. Medoff, Kailua, HI (US)

(73) Assignees: L. G. Tellman, Falsterbo (SE); David Medoff, Valencia, CA (US)

( * ) Notice: Subject to any disclaimer, the term of this patent is extended or adjusted under 35 U.S.C. 154(b) by 988 days.

(21) Appl. No.: 12/048,794

(22) Filed: Mar. 14, 2008

(65) Prior Publication Data
US 2008/0208261 A1 Aug. 28, 2008

Related U.S. Application Data

(62) Division of application No. 11/331,738, filed on Jan. 13, 2006, now abandoned.

(51) Int. Cl.
*A61B 17/56* (2006.01)
(52) U.S. Cl. .......... 606/64; 606/281; 606/86 R; 606/99
(58) Field of Classification Search .................. 606/60, 606/62–64, 67, 68, 86 R, 87, 89, 96, 98, 99, 606/104, 105
See application file for complete search history.

(56) References Cited

U.S. PATENT DOCUMENTS

| 583,455 A | 6/1897 | Bush |
|---|---|---|
| 3,763,855 A | 10/1973 | McAtee |
| 3,939,828 A | 2/1976 | Mohr et al. |
| 4,438,762 A | 3/1984 | Kyle |
| 5,013,314 A | 5/1991 | Firica et al. |
| 5,035,697 A | 7/1991 | Frigg |
| 5,197,966 A | 3/1993 | Sommerkamp |
| 5,372,604 A | 12/1994 | Trout |
| 5,472,444 A | 12/1995 | Huebner et al. |
| 5,620,445 A | 4/1997 | Brosnahan et al. |
| 5,653,709 A | 8/1997 | Frigg |

(Continued)

FOREIGN PATENT DOCUMENTS

SU 1175480 8/1985

(Continued)

OTHER PUBLICATIONS

Extended European Search Report dated May 4, 2007 in connection with counterpart foreign application, 8 pages.

*Primary Examiner* — Eduardo C Robert
*Assistant Examiner* — Ellen C Hammond
(74) *Attorney, Agent, or Firm* — Patzik, Frank & Samotny Ltd.

(57) ABSTRACT

An intramedullary implant, useful particularly for the fixation of fractures of the radius, the implant comprising a first and second end, both ends configured for entry into the intramedullary canal through an entry point on the bone, such as the fracture site, and configured for positioning within the intramedullary canal of the fractured bone, the first end positioned in the intramedullary space of a first bone fragment and the second end positioned in the intramedullary space of a second bone fragment on the opposite side of the fracture. The first end is positioned by displacing the implant in a first direction and the second end is positioned by displacing the implant in a second direction, substantially opposite to the first direction. The implant further comprises a tip configured to abut an end surface of the second fragment to provide axial support to second fragment.

14 Claims, 16 Drawing Sheets

U.S. PATENT DOCUMENTS

| | | |
|---|---|---|
| 5,658,287 A | 8/1997 | Hofmann et al. |
| 6,010,505 A | 1/2000 | Asche et al. |
| 6,033,407 A | 3/2000 | Behrens |
| 6,123,708 A | 9/2000 | Kilpela et al. |
| 6,302,884 B1 | 10/2001 | Wellisz et al. |
| 6,527,775 B1 | 3/2003 | Warburton |
| 6,562,042 B2 * | 5/2003 | Nelson ............... 606/62 |
| 6,730,090 B2 | 5/2004 | Orbay et al. |
| 6,793,659 B2 | 9/2004 | Putnam |
| 2004/0010255 A1 * | 1/2004 | Warburton .............. 606/62 |
| 2005/0070902 A1 | 3/2005 | Medoff |
| 2006/0015101 A1 * | 1/2006 | Warburton et al. ........ 606/62 |
| 2006/0264944 A1 * | 11/2006 | Cole ................... 606/62 |

FOREIGN PATENT DOCUMENTS

| | | |
|---|---|---|
| WO | WO9515728 | 6/1995 |

* cited by examiner

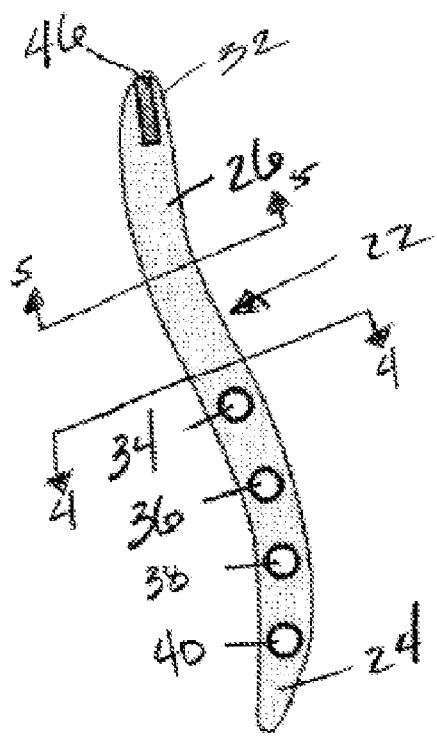
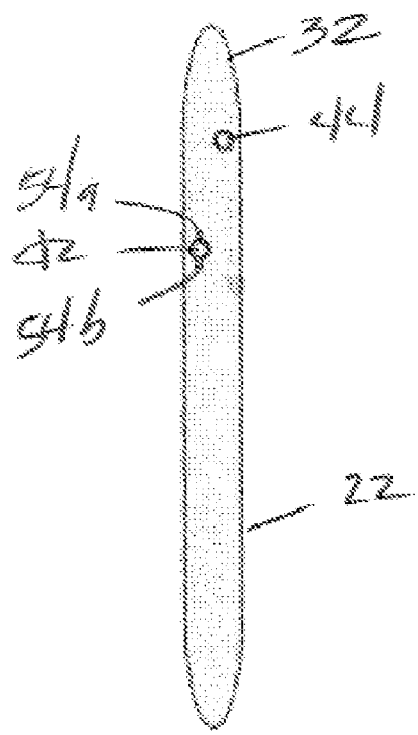
FIGURE 17
FIGURE 18
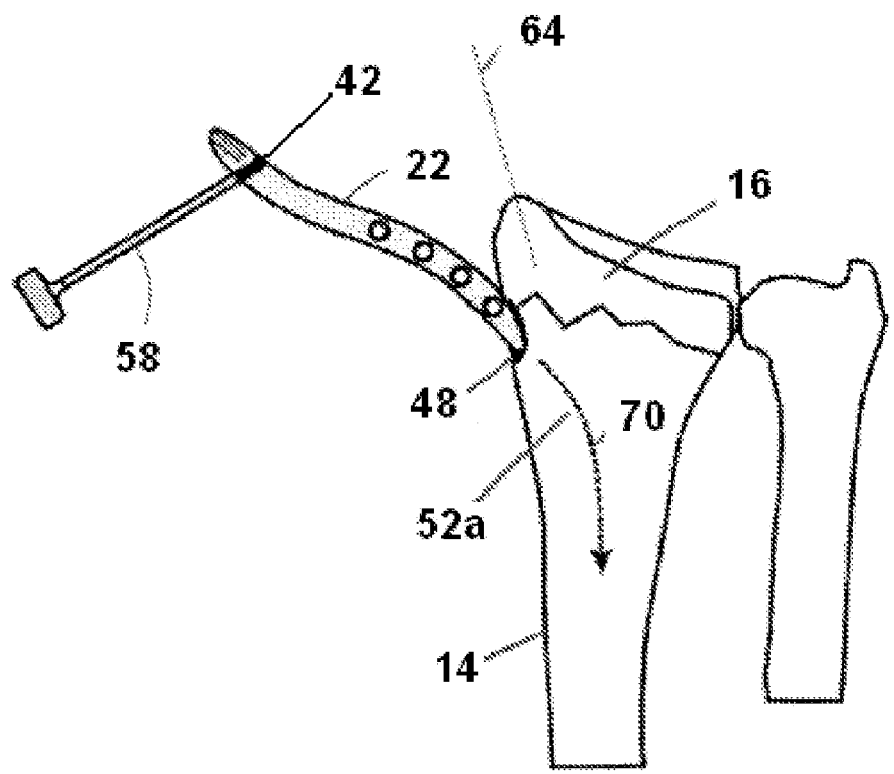
FIGURE 19

METHOD OF USING AN INTRAMEDULLARY IMPLANT FOR FRACTURE FIXATION

CROSS-REFERENCE TO RELATED APPLICATIONS

This application is a division of U.S. application Ser. No. 11/331,738, filed Jan. 13, 2006, the entirety of which is hereby incorporated by reference.

FIELD OF THE INVENTION

This invention relates to an intramedullary fracture fixation implant and particularly to a fracture fixation implant for fixation of distal fractures of the radius in which the implant is adopted to be axially inserted and secured within the intramedullary canal portions of the bone segments on opposing sides of the fracture. The invention further comprises a method of fracture fixation with the intramedullary fracture fixation implant of the present invention.

BACKGROUND AND PRIOR ART

Fractures that occur in proximity to a joint can be difficult to treat. Although plates, screws and pins on the surface of the bone can provide fracture stability, often the close proximity of tendons to the surface of the bone can result in soft tissue irritation and even tendon rupture that can compromise the outcome. Intramedullary fixation of fractures, with or without cross-locking screws, is well known to reduce the problem of soft tissue irritation by placing the bulk of the implant within the bone itself.

Furthermore, intramedullary fixation can provide fracture stability because of either a tight fit of the rod within the bone or fixation from locking screws that cross through the bone and rod. Traditional intramedullary rods, however, are not well suited for fixation of a fracture in proximity to the end of the bone. For example, in the case of fractures of the distal radius, the distal end of the radius is extremely wide with soft cancellous bone within the intraosseous space and only thin weak cortical bone that surrounds the tubular structure; the strongest bone at the distal end of the radius is the thick subchondral bone that extends behind the articular surface and is under the tip of the radial styloid. In the case of fractures of the distal radius, insertion of the implant is not possible through the tubular proximal fragment because of its deep location and the narrow, cylindrical nature of the morphology that makes it impossible to direct an intramedullary implant down the center of the bone. Because of this, intramedullary fixation of distal radius fractures has always inserted the device directly through the soft radial surface of the radial styloid in order to direct the implant within the intramedullary canal. This necessarily results in creation of a large additional hole that is at least the diameter of the implant in the small distal fragment, which can easily result in creation of additional fragmentation, collapse of the fragment and resultant loss of fixation.

In addition, since the implant is inserted through this large defect in the distal fragment, it is not possible for the end of the implant to be used to provide axial support to the fragment; instead, the implant is totally dependent on the resistance of the thin cortical bone to translational movement and the purchase of transverse locking screws in the soft, often osteoporotic, metaphyseal bone. As a result, loss of radial length can easily occur, resulting in protrusion of the nail from the insertion site as well as deformity and loss of function. Finally, because the end of the bone is often covered with articular cartilage which is damaged if a nail is inserted through it, standard intramedullary implants are unable to provide support to the end of the bone as they must be placed more proximal to this area to prevent damage to the joint.

Standard intramedullary rods use cross locking screws to prevent the small distal fragment from losing length. Examples of standard intramedullary rods are shown in U.S. patent application Ser. No. 10/377,255 to Warburton and entitled Intramedullary Interlocking Fixation Device for the Distal Radius (U.S. Publication No. 2004/0010255) and U.S. patent application Ser. No. 09/975,514 to Putnam and entitled Intramedullary Rod for Wrist Fixation (U.S. Publication No. 2003/0073999). Because these screws are placed across the nail into the metaphyseal bone of the distal fragment, they are loaded at their tip by the compressive loads that occur across the wrist. This places a significant torque on the screw, which can lead to increased implant loads and can result in breakage, cutout through the bone, or loosening of the screw. In turn these can result in loss of length, deformity, and impaired function of the wrist.

Since the distal radius is made of relatively soft cancellous bone, there is little resistance to side-to-side translational displacements by a standard intramedually nail, particularly since the nail is placed through a hole made in the bone and courses to lie entirely within the metaphyseal cavity. This results in poor support of the fragment by the nail itself, requiring the majority of resistance to displacement to be taken up by the distal crossing screws.

In copending U.S. patent application Ser. No. 10/675,864 to Medoff and entitled Intramedullary Implant for Fracture Fixation (U.S. Publication No. 2005/0070902), an approach was described that provides axial support of the radial styloid by the tip of an implant that is placed intramedullary into the distal fragment. Since the implant lies on the extraosseous surface proximally, the implant enters the fracture site and can be placed with a single longitudinal insertion into the distal fragment. However, this design requires a more extensive dissection for placement of the extramedullary portion of the implant in addition to resulting in an implant that is still fixed on the surface of the bone over one part, with the possibility of further soft tissue irritation. In addition, since the surface portion of the implant must be thin to avoid prominence and soft tissue irritation, this creates a stress riser at the junction of the extramedullary and intramedullary portions of the implant that can result in breakage.

Current intramedullary implants are inserted into a tubular bone from one end and driven to the opposite end. In some applications, the implant is inserted at the proximal end of the bone and driven in an ante grade direction into the distal end of the long bone. In other applications, the implant is inserted at the distal end of a long bone and driven in a retrograde direction into the proximal end. Because the direction of insertion is always uni-directional, current intramedullary designs do not permit fixation both above and below the site of insertion of the implant. In addition, since existing intramedullary implants are designed for insertion in a single direction only (either ante grade or retrograde), these implants are always connected to a driver at one end.

SUMMARY OF THE INVENTION

An object of the current invention is to provide an intramedullary implant that can be inserted without the creation of a new, large defect in either fragment, but particularly the small distal fragment, thereby avoiding the risk of additional fracture comminution caused from the insertion procedure itself.

A further object of the invention is to provide an intramedullary implant that can be inserted without the necessity of driving the implant along a single axis into the bone from one end, thereby avoiding the problem of positioning the insertion hole in the bone directly over the end of the implant and resulting in the inability of the implant to support the distal fragment axially and poor resistance to shortening.

A further object of the invention is to provide an intramedullary implant that resists loss of length by providing axial support along its tip to the strong subcortical bone at the end of a fragment.

A further object of the invention is to provide an intramedullary implant that can both resist loss of length through axial support of an unstable bone fragment as well as achieve rotational support from cross locking screws in the unstable fragment.

A further object of the invention is to allow a provision for a relatively smooth tip to be situated centrally within the conical morphology of the tip of the radial styloid, abutting the strong subchondral surface at the end of the bone. In addition to the load support by the tip, the tip is captured by the concave conical bone at the radial styloid, thereby resisting translational movement of the distal fragment by the nail itself. This is comparable to the way a tent is supported by a tent pole.

A further object of the invention is to provide a method of fixation that is simple to apply, allows insertion of an intramedullary implant to span a fracture defect by insertion of the implant through the fracture site itself, with a minimal incision or even subcutaneous approach.

A further object of the invention is to provide instrumentation that allows an intramedullary implant to be inserted through a fracture defect into an intramedullary position, spanning the fracture defect and achieve purchase in the fragments on both sides of a fracture.

A further object of the invention is to provide a means of insertion that allows an intramedullary implant to be inserted in one direction through a relatively central insertion site in the bone, and then displaced in the opposite direction to allow bone purchase on both sides of the insertion site.

A further object of the present invention is to provide instrumentation that cooperates with areas of connection on an intramedullary implant in order to allow the implant to be axially displaced in a direction that is opposite of the initial insertion of the implant into the bone.

BRIEF DESCRIPTION OF THE DRAWINGS

FIG. 17 is a front elevation view of another preferred embodiment of an intramedullary fixation device according to the present invention;

FIG. 18 is a side elevation view of another preferred embodiment of an intramedullary fixation device according to the present invention;

FIG. 19 is a schematic view of a step in a method for fixing a bone fracture using the intramedullary fixation device of the present invention;

DETAILED DESCRIPTION OF THE DRAWINGS

Figure 1:
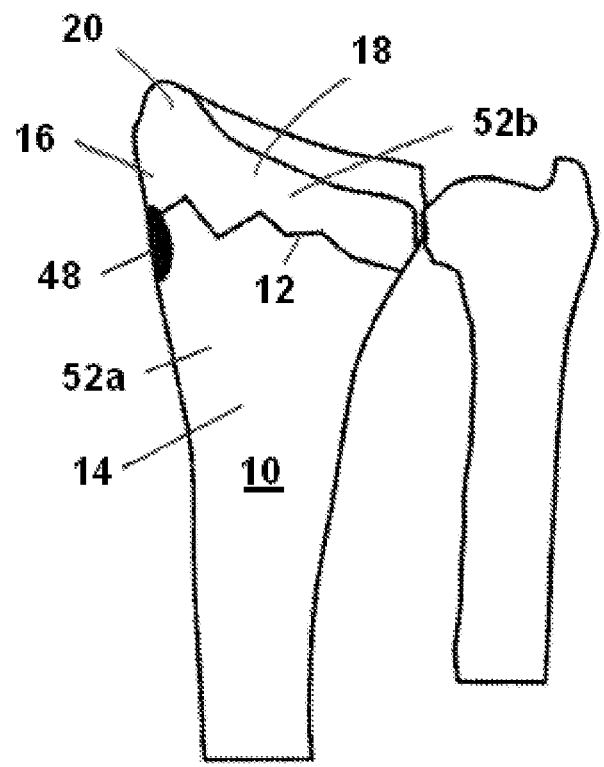
FIG. 1 is a schematic view of a step in a method for fixing a bone fracture using the intramedullary fixation device of the present invention.

In accordance with the present invention, a fracture fixation device is provided which comprises an intramedullary rod for placement into a fracture defect. Referring to FIG. 1, a bone 10, such as the radius, is shown in which a fracture 12 is present at its distal end and forms a stable first, proximal bone fragment 14, and an unstable second, distal bone fragment 16. The second bone fragment 16 has an end portion 18, comprising, for example, the radial styloid 20 when the fracture is a distal radius fracture. The fracture 12, as illustrated in FIG.

1, is in proximity to the end portion 18 of the second fragment 16 of the bone 10. However, the fracture can also be displaced proximally or centrally on the bone without altering the inventive concept. It should also be noted that the general design of the present fracture fixation implant is applicable to other locations, such as the end of the humerus, ulna, tibia, fibula, femur or other long bones comprising an intramedullary canal, without restricting the spirit or scope of the invention.

Figure 2:
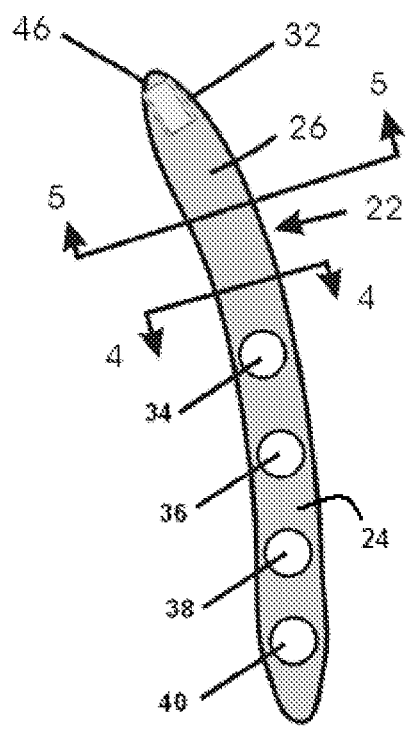
FIG. 2 is a front elevation view of the intramedullary fixation device according to the present invention.
Figure 3:
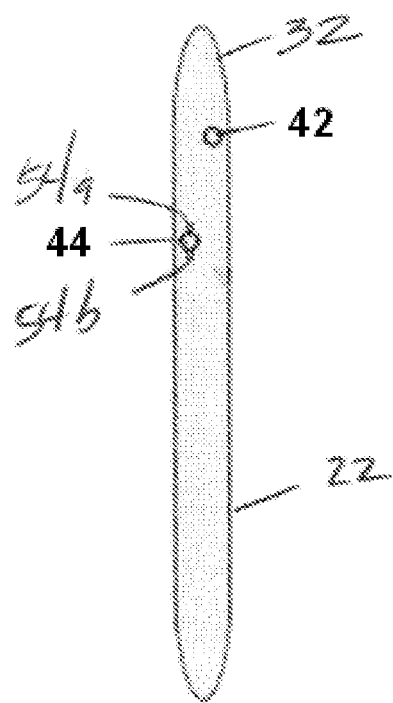
FIG. 3 is a side elevation view of the intramedullary fixation device according to the present invention.

Referring to FIGS. 2-5, an intramedullary fracture fixation implant 22 is shown. The implant 22 comprises a first end 24 and a second end 26. In the embodiment of the present invention shown in FIG. 2, the implant 22 is largely banana-shaped and has a curvilinear profile when viewed from the anterior-posterior view and a generally linear profile when viewed from the lateral view (FIG. 3). The implant 22 is composed of any suitable material that exhibits the appropriate mechanical and biological compatibility with the fraction fixation. In a preferred embodiment, the implant is composed of surgical grade stainless steel, surgical grade titanium, or a surgical grade titanium alloy. In other preferred embodiments, any surgical grade implantable material with sufficient strength and stiffness characteristics can be used.

The first end 24 of the implant 22 may comprise at least a first receptor configured to receive a fastener for securely and releasably mating the implant to the shaft of the bone 10. In the embodiment of the present invention shown in FIG. 2, a plurality of receptors 34, 36, 38, 40, are used, each of the plurality of receptors comprising a screw hole having an open-ended channel extending across the width of the first end 24 of the implant 22. The number of receptors required can vary and is dependent on the particular application for the implant and desired or required amount of the fixation of the first end to the first fragment.

Figure 4:
FIG. 4 is a cross-section view of the intramedullary fixation device according to the present invention taken along section line 4-4 in FIGS. 2 and 17.

In a preferred embodiment, the cross section of the first end 24 is in the form of a square with curved corner portions (FIG. 4). The first, second, third, and fourth screw holes 34, 36, 38, 40 are all disposed on the same surface of the implant 22. This configuration enables the insertion of fasteners into the receptors from a dorsal approach, enabling avoidance of tendons, nerves, or major arteries in the area. The fasteners are captured by and extend through the receptors 34, 36, 38, 40 and into the shaft of the first fragment 14 (FIG. 1) to the secure the implant 22 to the bone 10. The modified square cross-section also assists in centering a fastener into a corresponding receptor.

It is also contemplated that the first end 24 can be formed into a square or circular cross-section. In addition, a means for self-centering the fasteners may be incorporated with each receptor, such as a counter bore surrounding each receptor or a concave entry portion for each receptor. In addition, in other preferred embodiments of the present invention, the receptors are disposed radially around the perimeter of the first end 24. Alternatively, receptors 34, 36, 38, 40 can be angled medial to lateral, arranged in an oblique orientation, or a combination of these configurations. The number of receptors may also vary to provide for secure fixation of a longer fracture, or a smaller implant for simplified fixation in simple fractures.

In the embodiment of the present invention shown in FIG. 2, the receptors 34, 36, 38, 40 are threaded and are configured to receive and capture fasteners comprising bone screws. However, it is contemplated that unthreaded receptors 34, 36, 38, 40 can be utilized without affecting the performance of the implant 22. When the receptors 34, 36, 38, 40 are unthreaded, it is contemplated that the fasteners comprise a peg, rivet, screw, or any other suitable fastener for engaging an unthreaded receptor.

The second end 26 of the implant 22 has a substantially round cross-section (FIG. 5) and may comprise a longitudinal receptor 46 at the tip 32 for receiving and capturing a fastener configured to mate the implant to the strong cortical bone at the end portion 18, and specifically in the radial styloid 20 of the second fragment 16 when the implant 22 is used in the fixation of a distal radius fracture. In accordance with the intended placement of the tip 32 of the implant 22, the tip 32 is contoured to largely conform to the contour of the endosteal surface of the radial styloid 20 of the radius 10. In addition, the surface contour of the tip 32 is large enough to spread the axial load on the implant at the tip 32 over a large contact area. This provides excellent support and strength to the second fragment 16 to resist loss of length of the bone 10 during the healing of the fracture, as well as the biomechanical advantage of avoiding excessive loading on the implant 22, that could result in breakage or cut-out.

This is in contrast to a standard intramedullary implant, in which the resistance to loss of length is borne by bone screws that extend through the width of the implant and are subject to high torque and implant loads that may lead to failure of the implant. In addition to its axial loading function or end-bearing function, the tip 32 is further configured to comprise a leading edge for driving the implant into position within the intramedullary space 52b of the bone 10. When the implant 22 is used for fracture fixation in bones other than the radius, the tip 32 is configured to largely conform to the endosteal surface or end portion of the second fragment of the bone to be fixed by the implant 22.

Figure 14:
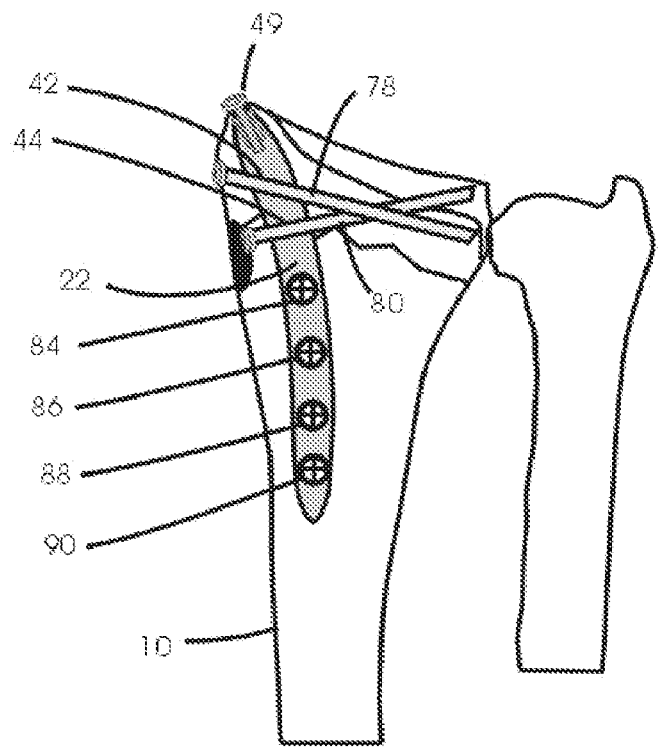
FIG. 14 is a schematic view of a step in a method for fixing a bone fracture using the intramedullary fixation device of the present invention.

The longitudinal receptor 46 comprises a threaded screw hole comprising an aperture and threaded channel bored into the tip 32. In the preferred embodiment of the present invention, the longitudinal fastener is a radial styloid bone screw 49 (FIG. 14). However, other suitable fasteners may also be used. The diameter of the second end 26 of the implant is significantly larger than the diameter of the longitudinal receptor 46 in order to allow the implant to support axial loading at the tip 32 during fracture reduction and fixation. After placement of the second end 26 of the implant 22 within the intramedullary space 52b and abutment of the tip 32 against the endosteal surface of the cortical bone of the radial styloid 20 (FIG. 1), the longitudinal fastener 49 (FIG. 14) is used to hold the implant in position against the cortical bone of the radial styloid 20.

Figure 15:
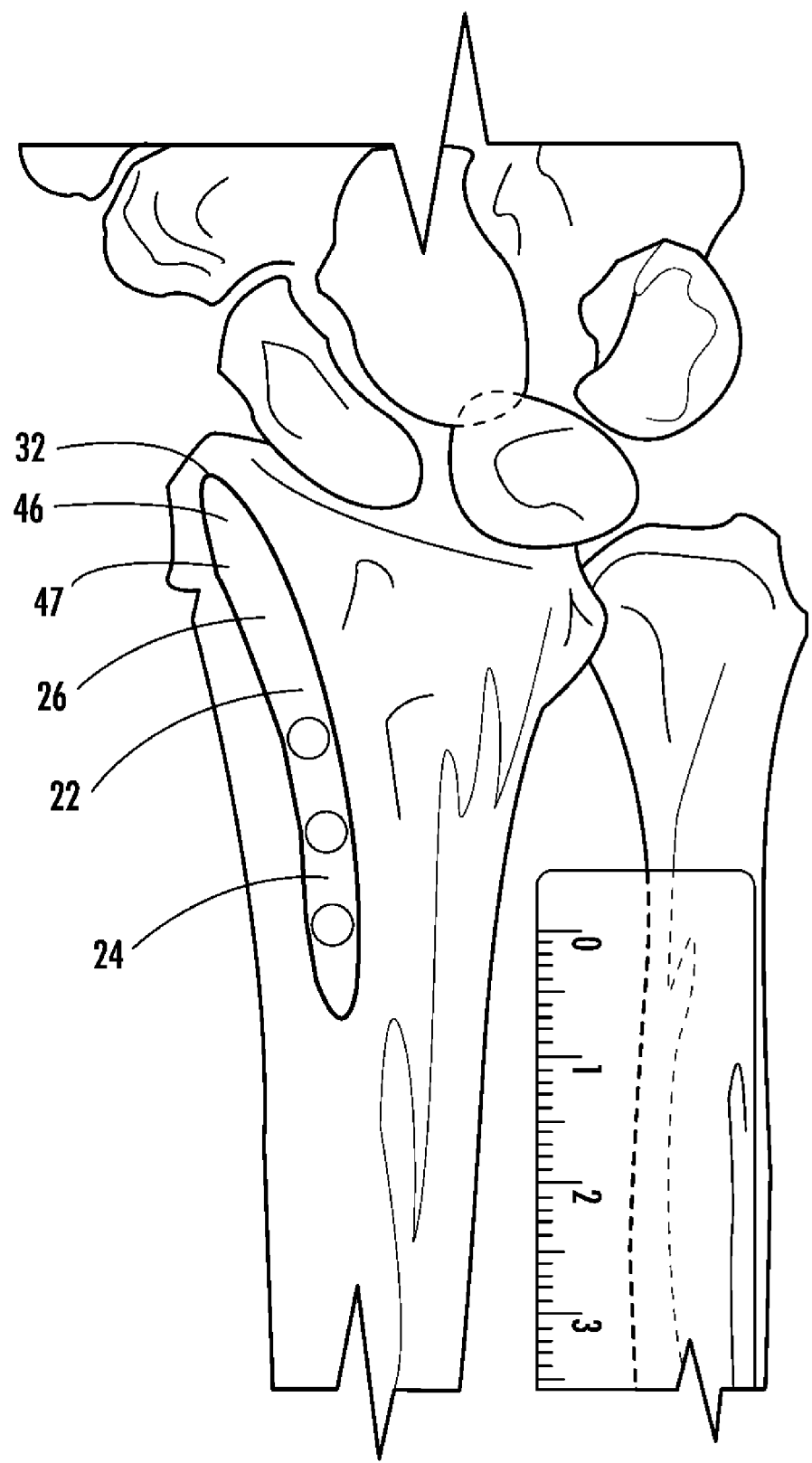
FIG. 15 is a schematic view of an x-ray showing the intramedullary fixation device of the present invention inserted within an intramedullary canal.

As is seen in FIG. 15, the tip 32 may also comprise a cannulated channel 47 that extends from the tip 32 through a segment of the second end 26 of the implant 22. The channel 47 is configured to receive and enable passage of a guide wire 64 (FIG. 16) from the radial styloid 20 of the second fragment 16 to guide the implant 22 into proper position. The cannulated channel 47 is integrally formed and coaxially aligned with the longitudinal receptor 46. However, the cannulated channel 47 may also be formed independent of the longitudinal receptor 46.

In the preferred embodiment of the present invention, the second end 26 may also comprise at least one cross-locking receptor for securely and releasably mating the implant 22 to the second fragment 16. In the embodiment shown in FIG. 3, a first and second cross-locking receptor 42, 44 are used for receiving and capturing a fastener. Each receptor 42, 44 comprises a screw hole having an open-ended channel extending diametrically through the second end 26 of the implant 22. The cross-locking receptors 42, 44 are preferentially, but not necessarily, radially spaced apart at an angular distance from each other. In one embodiment, the cross-locking receptor 42 is directed volarly at angle of approximately 17 degrees to the palm in respect to the coronal plan, and is approximately 10 degrees proximally inclined. The cross-locking receptor 44 is directed dorsally at an angle of approximately 12 degrees with respect to the coronal plan and is approximately 8 degrees proximally inclined. However, this specific angular displacement of the cross-locking receptors 42, 44 is disclosed for exemplary purposes only. This arrangement enables engagement of the volar subchondral bone of the second fragment 16 by a fastener that is captured by and extending through the first receptor 42 and engagement of the dorsal subchondral bone of the second fragment 16 by a fastener that is captured by and extends through the second receptor 44.

Referring to FIGS. 1, 6-7, and 10-12, the implant 22 is also provided with a radial driver assembly configured to attach a driver 58 or alignment jig to the implant 22 to facilitate insertion of the implant 22 through an entry point 48 on the bone 10 and into the intrameduallary space 52a of the first fragment 14, and to allow for positioning of the implant 22 within the intramedullary space 52a. In a preferred embodiment of the present invention, the cross-locking receptor 42 is also configured to releasably capture the driver 58, as will be described below. The externally threaded end 60 of the driver 58 releasably engages the corresponding internal threads in the receptor 42 to provide a handle for insertion of the implant 22 into the intramedullary space 52a. In other preferred embodiments, the driver can take the form of a peg that is received by a corresponding receptor on the second end 26, or alternatively, the driver can include a tongue-like end that is received by a groove in the second end 26.

An axial driver assembly is provided to enable the implant to be displaced across the fracture site 12 from the first intramedullary space 52a into the intramedullary space 52b of the second fragment 16 until the tip 32 abuts the end portion 18 of the second fragment 16, e.g. the endosteal surface of the radial styloid 20 when the implant 22 is used during fixation of a distal radius fracture. In the first preferred embodiment of the present invention, the longitudinal receptor 46 is also configured to receive and capture a driver 50 (FIG. 6) or alignment jig to facilitate drawing the implant into the intramedullary space 52b. The externally threaded end 56 of the driver 50 releasably mates with the corresponding internal threading of the longitudinal receptor 46.

Figure 12:
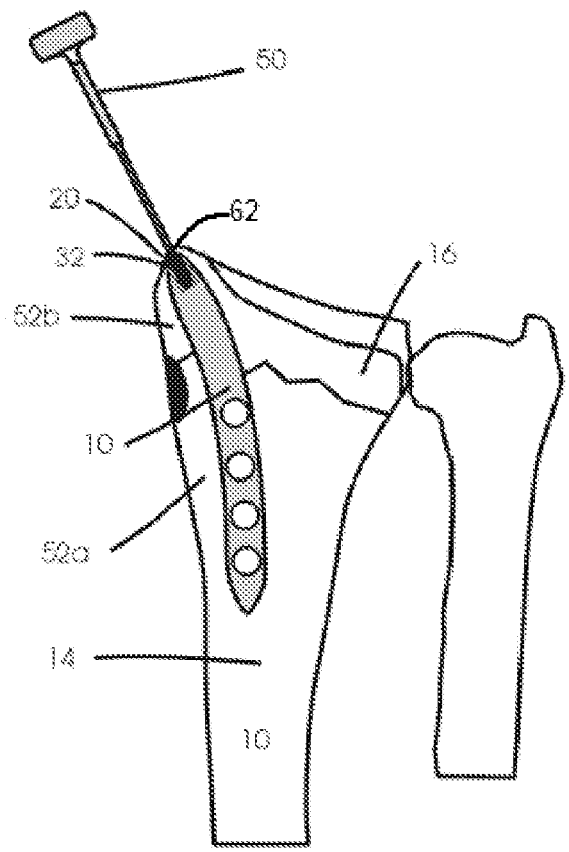
FIG. 12 is a schematic view of a step in a method for fixing a bone fracture using the intramedullary fixation device of the present invention.

The driver 50 is used as a handle to draw the implant 22 towards the radial styloid 20 (FIG. 12). The driver 50 has a section of reduced diameter above the terminal thread enabling angular adjustment of driver 50 within the hole drilled through the radial styloid 20 to enable alignment of the driver tip 56 with the threads in longitudinal receptor 46 and to allow the two pieces to be connected and screwed together. Once the implant is in position, the driver 50 is removed from the longitudinal receptor 46 and can be replaced by a fastener, such as a radial styloid screw, as described above. In other preferred embodiments, the driver can take the form of a peg that is received by a corresponding receptor on the second end 26, or alternatively, the driver can include a tongue-like end that is received by a groove in the tip 32.

Figure 5:
FIG. 5 is a cross-section view of the intramedullary fixation device according to the present invention taken along section line 5-5 in FIGS. 2 and 17.
Figure 6:
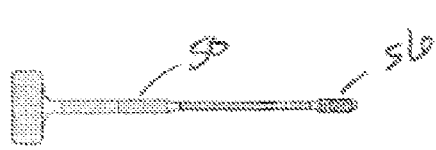
FIG. 6 is an elevation view of a component of the intramedullary fixation device of the present invention.
Figure 7:
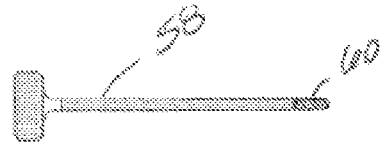
FIG. 7 is an elevation view of a component of the intramedullary fixation device of the present invention.

FIGS. 17 and 18 show a second preferred embodiment of the present invention wherein the general shape of implant 22 is S-shaped (FIG. 17) when viewed from the anterior-posterior view and generally linear when viewed from the lateral view (FIG. 18). As is shown in FIGS. 4 and 5, the implant of the second preferred configuration has the same cross-sectional geometry as the banana-shaped implant previously described. The use and configuration of: at least a first receptor, and preferably a plurality of receptors 34, 36, 38, 40, disposed on the first end 24 of the implant 22; zero, one or more cross-locking receptors at the second end 26 of the implant 22, and preferably a plurality of cross-locking receptors 42, 44; a longitudinal receptor 46 at the tip 32 of the second end 26; and receptors for axial and radial driver assemblies is also the same as described above.

FIGS. 1, 8-15, and 19-24 show a method of the using the intramedullary fracture fixation implant 22 of both the first and second preferred embodiments of the present invention for reduction and fixation of a distal radius fracture. The same methodology may be used to reduce and fix fractures of bones other than the radius. First, an entry site 48 for the implant 22 is formed in the bone 10. In FIG. 1, a biting tool or reamer (not shown) is used to extend an opening 48 from the fracture site 12 proximally to allow insertion of the implant 22. While extending the opening 48 from the fracture site 12 extends the already unstable fracture site, it does not add a new hole in the first fragment 14. Accordingly, its effect on weakening the bone 10 is relatively minor. In addition, no additional defect is created in the small, peri-articular distal fragment 16 as would occur if a traditional insertion technique from the end of the bone was used. In other embodiments of the invention, a new point of entry 48 of the implant into the intramedullary canal 52 may be formed in the bone 10.

Figure 8:
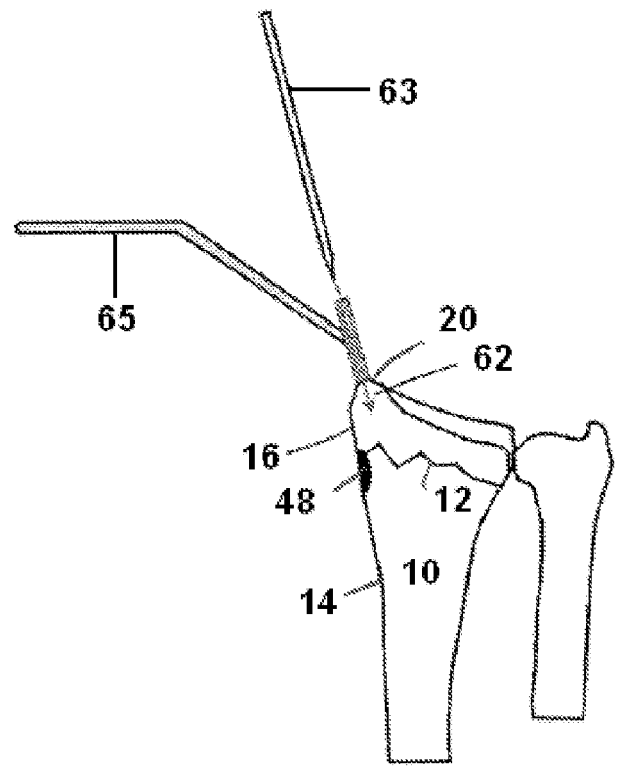
FIG. 8 is a schematic view of a step in a method for fixing a bone fracture using the intramedullary fixation device of the present invention.
Figure 9:
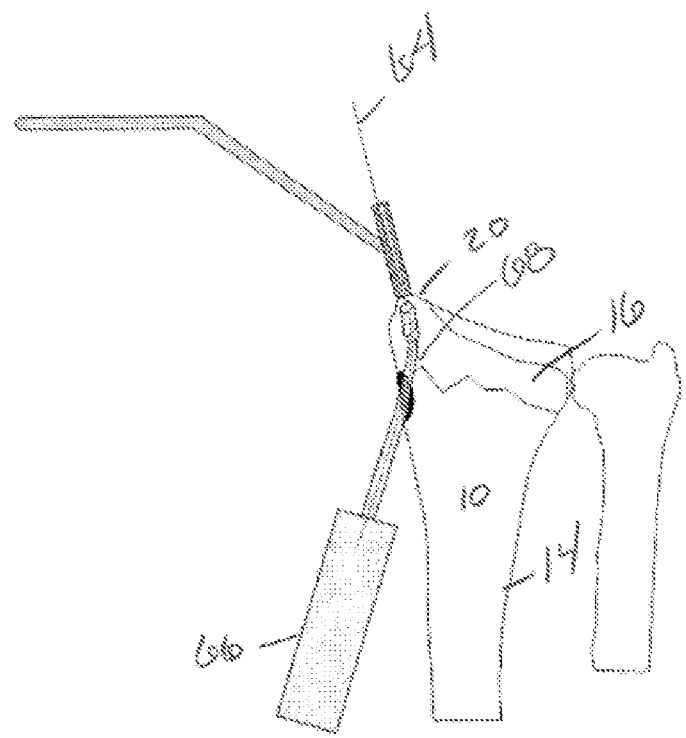
FIG. 9 is a schematic view of a step in a method for fixing a bone fracture using the intramedullary fixation device of the present invention.
Figure 16:
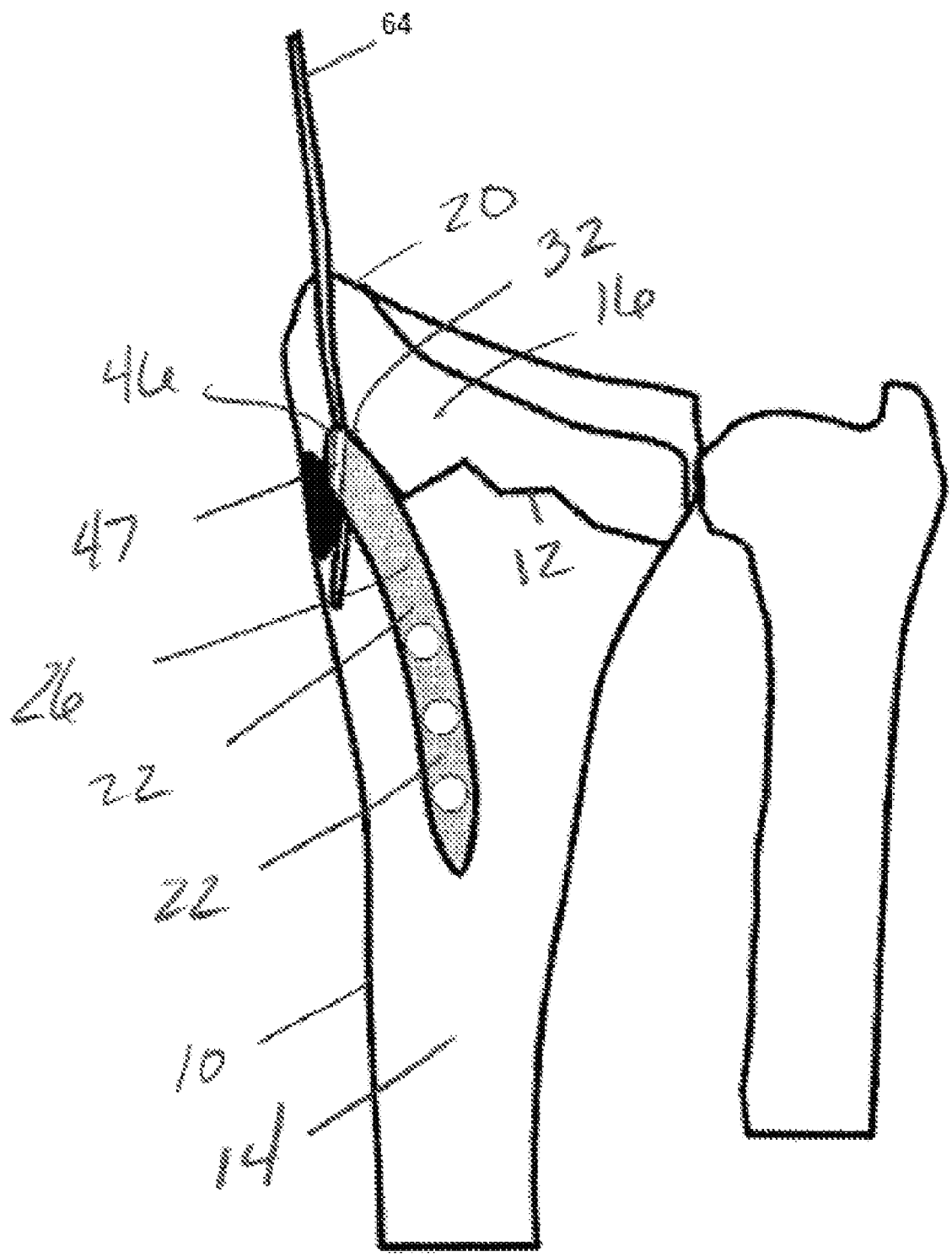
FIG. 16 is a schematic view of a step in a method for fixing a bone fracture using the intramedullary fixation device of the present invention.

As is shown in FIG. 8, an aperture 62 is then formed in the tip of the radial styloid 20 of the second fragment 16. The aperture 62 is formed by a drill, awl or pin 63. A guide 65 may also be used to confirm the positioning of the drill, awl, or pin 63 at the proper entry location and to prevent wrapping of soft tissues structures as the aperture 62 is formed. The aperture 62 is at least of a diameter to accommodate the driver 50 (FIG. 6) and longitudinal fastener 49 (FIG. 14) that are received and captured by the longitudinal receptor 46, as was described previously; typically this may range in size between 0.5 mm to 5 mm. If required, a guide wire or ribbon 64 is inserted through the aperture 62 and into the intramedullary space 52b (FIG. 9). As is seen in FIG. 16, the guide wire or ribbon 64 is received by the cannulated channel 47. FIG. 9 also shows the use of an impactor or cannulated flexible reamer 66 to develop a pathway in the intramedullary space 52b of the second fragment 16. A path 68 through the soft metaphyseal bone is made to enable abutment of the tip 32 of the implant 22 against the strong subchondral bone surface of the radial styloid 20.

Figure 10:
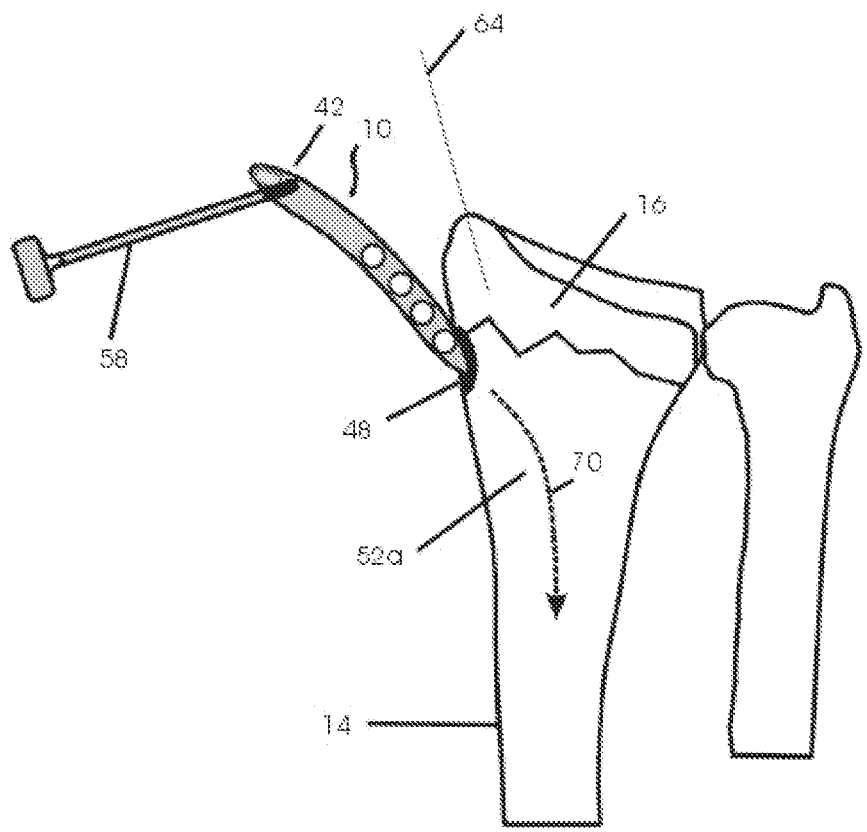
FIG. 10 is a schematic view of a step in a method for fixing a bone fracture using the intramedullary fixation device of the present invention.
Figure 11:
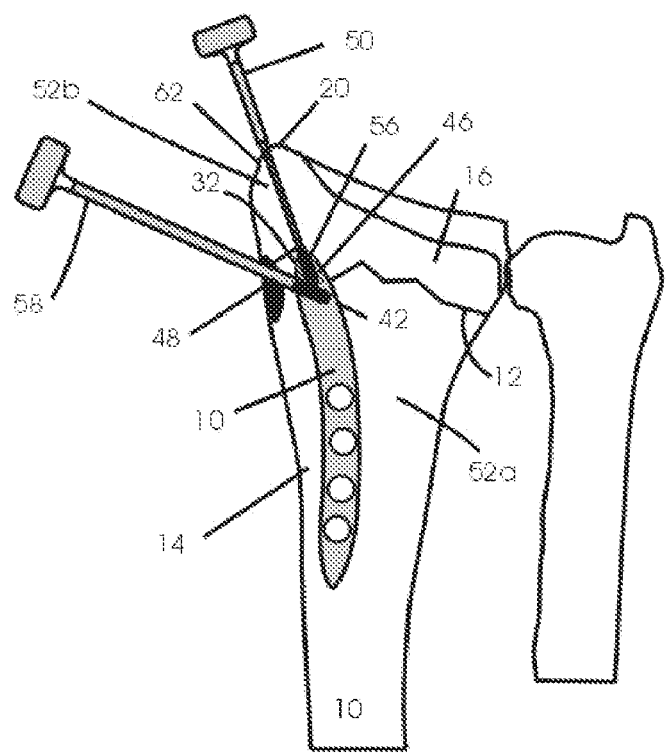
FIG. 11 is a schematic view of a step in a method for fixing a bone fracture using the intramedullary fixation device of the present invention.
Figure 20:
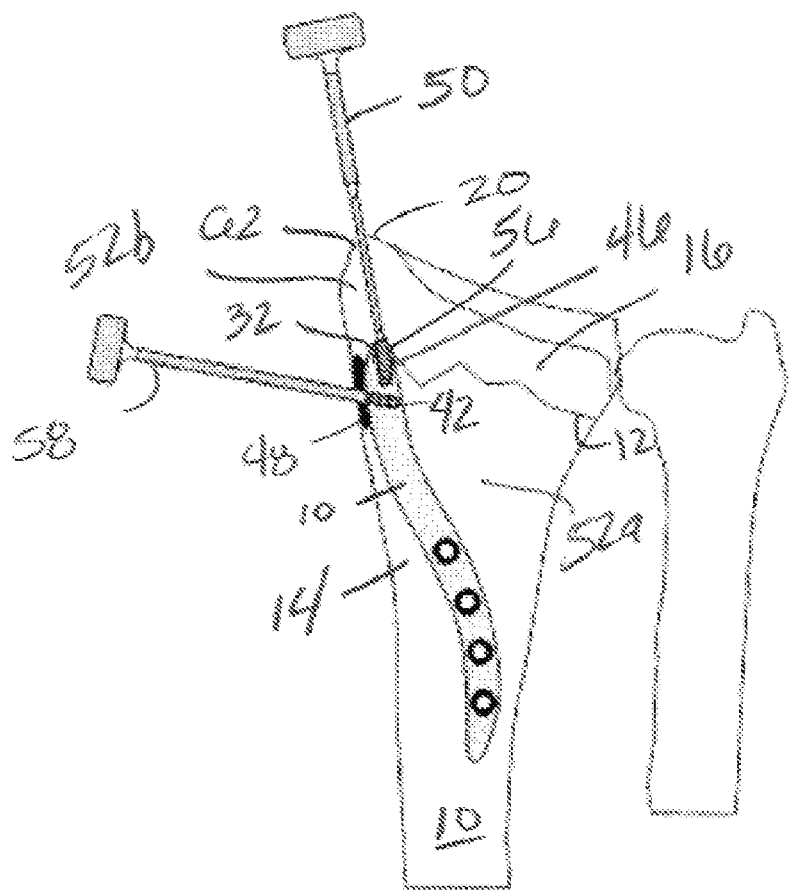
FIG. 20 is a schematic view of a step in a method for fixing a bone fracture using the intramedullary fixation device of the present invention.

Next, as is shown in FIGS. 10 and 19, a driver 58 or alignment jig is releasably mated with the implant 22 at the cross-locking receptor 42 and the implant 22 is inserted through the entry point 48 into the intramedullary space 52a of the first fragment 14. As shown in FIGS. 11 and 20, once the implant 22 is inserted into the intramedullary space 52a, the second driver 50 is inserted through the aperture 62 in the radial styloid 20, through the path 68, and is releasably mated with the implant at the longitudinal receptor 46 in the tip 32. The driver 58 can be used to stabilize the implant and prevent rotation of the implant 22 as the driver 50 is screwed into place. The driver 58 or alignment jig is then removed from the cross-locking receptor 42 to enable the implant to be displaced across the fracture site 12.

Figure 21:
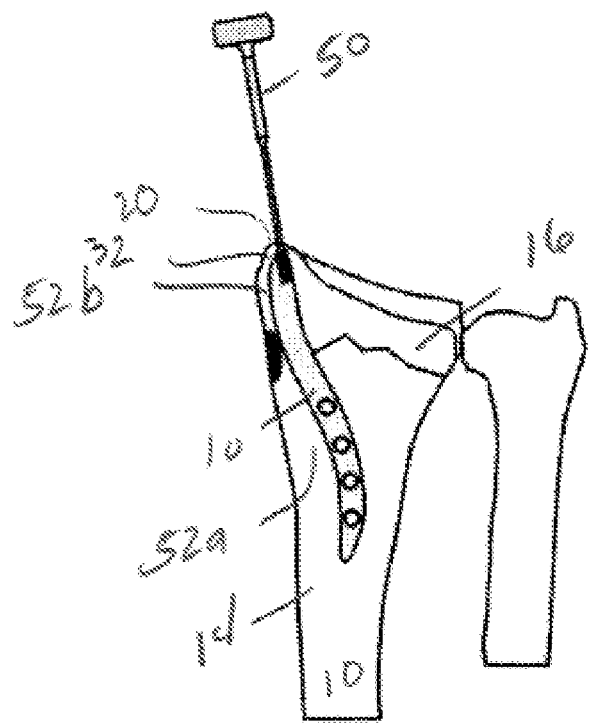
FIG. 21 is a schematic view of a step in a method for fixing a bone fracture using the intramedullary fixation device of the present invention.

Referring to FIGS. 12 and 21, the implant 22 is then drawn into the intramedullary space 52b of the second fragment 16 until the tip 32 of the implant 22 abuts the endosteal surface of the subchondral bone under the radial styloid 20. Since the tip 32 is larger than the aperture 62 in the radial styloid 20, the tip 32 of the implant provides axial support to maintain radial length without the obligate torque that occurs when the resistance to loss of radial length is provided exclusively by cross fixation members. In addition, the congruence of the surface contour of the tip 32 to the endosteal surface of the radial styloid 20 adds further constraint to resist side-to-side movement of the second fragment 16. As is seen in these figures, the implant 22 is positioned with the intramedullary space 52*a* of the first fragment 14 by displacing the first end 24 in a first direction and then displacing the implant in a second direction, substantially opposite the first direction, to place the second end 26 into the intramedullary space 52*b* of the second fragment 16.

Figure 13:
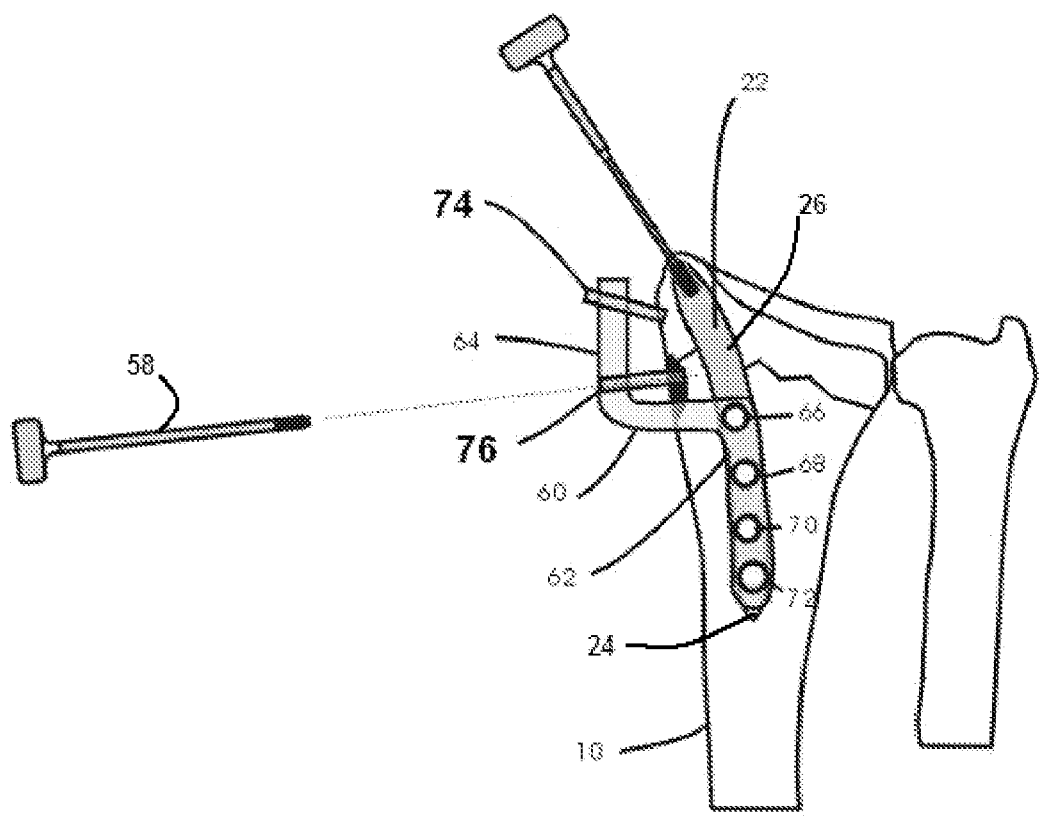
FIG. 13 is a schematic view of a step in a method for fixing a bone fracture using the intramedullary fixation device of the present invention.
Figure 22:
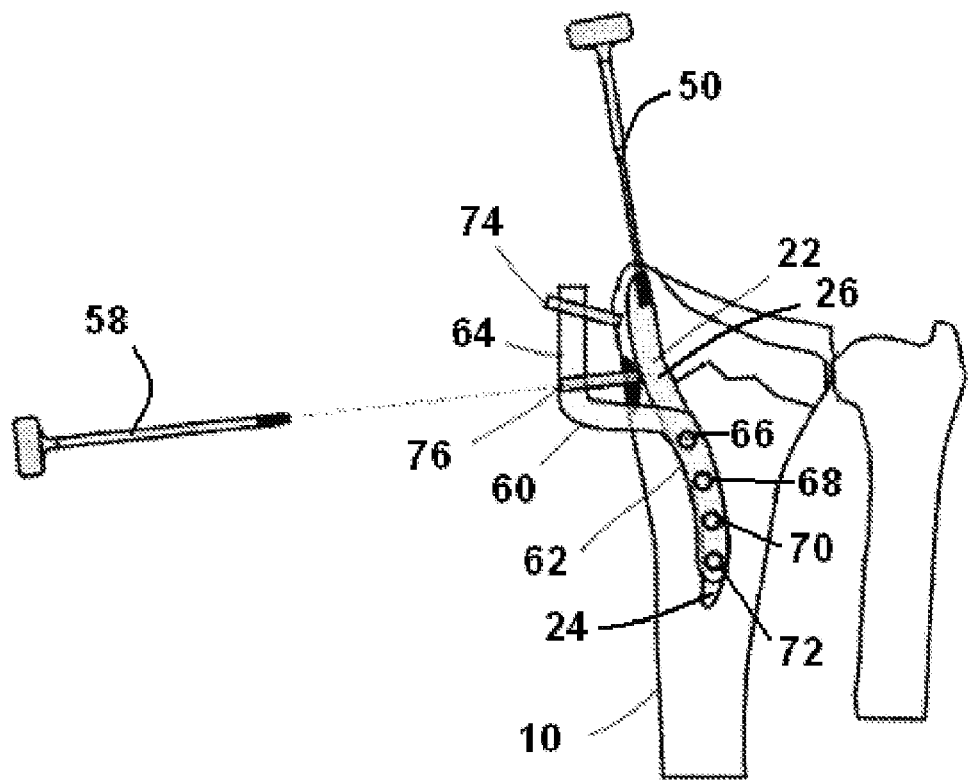
FIG. 22 is a schematic view of a step in a method for fixing a bone fracture using the intramedullary fixation device of the present invention.

As is shown in FIGS. 13 and 22, the implant 22 is positioned at the proper angular position and a drill guide 60 having a first and second end 62, 64 is positioned where the first end 62 of the drill guide 60 overlaps the first end 24 of the implant 22 on the exterior of the bone 10 and the second end 64 of the drill guide 60 is aligned with the second end 26 of the implant 22. The first end 62 of the drill guide 60 comprises apertures 66, 68, 70, 72 that align with the receptors 34, 36, 38, 40 at the first end 24 of the implant 22. The second end 64 comprises drill guides 74, 76 that may be used to bore holes in the bone 10 and/or form the cross-locking receptors 42, 44.

In one embodiment, the implant 22 may comprise an alignment mechanism to orientate the drill guide 60 and align apertures 66, 68, 70, 72 and receptors 34, 36, 38, 40 and properly position the drill guides 74, 76. As shown in FIGS. 3 and 18, the orientation mechanism for the alignment jig may be integrally formed with one of the cross-locking receptors 42 when the cross-locking receptors 42, 44 are formed in the implant 22 prior to insertion of the implant within the bone 10 and comprises diametrically spaced slots on 54*a*, 54*b* opposing sides of the cross-locking receptor 44. Alternatively, the orientation mechanism may be a receptor on the side of the implant or may be attached to second driver 58.

Drilling holes into the bone through the apertures 66, 68, 70, 72 will form concentric channels with the receptors 34, 36, 38, 40 for receiving fasteners to secure the implant 22 to the first fragment 14. The first guide 74 is used to bore the first receptor 42 into the second end 26, and the second guide 76 aligns to form the second receptor 44.

Figure 23:
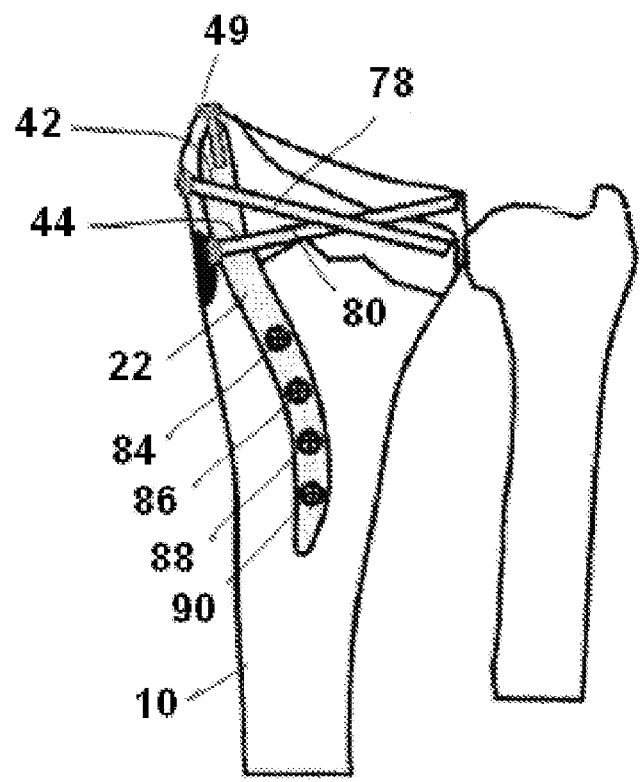
FIG. 23 is a schematic view of a step in a method for fixing a bone fracture using the intramedullary fixation device of the present invention.
Figure 24:
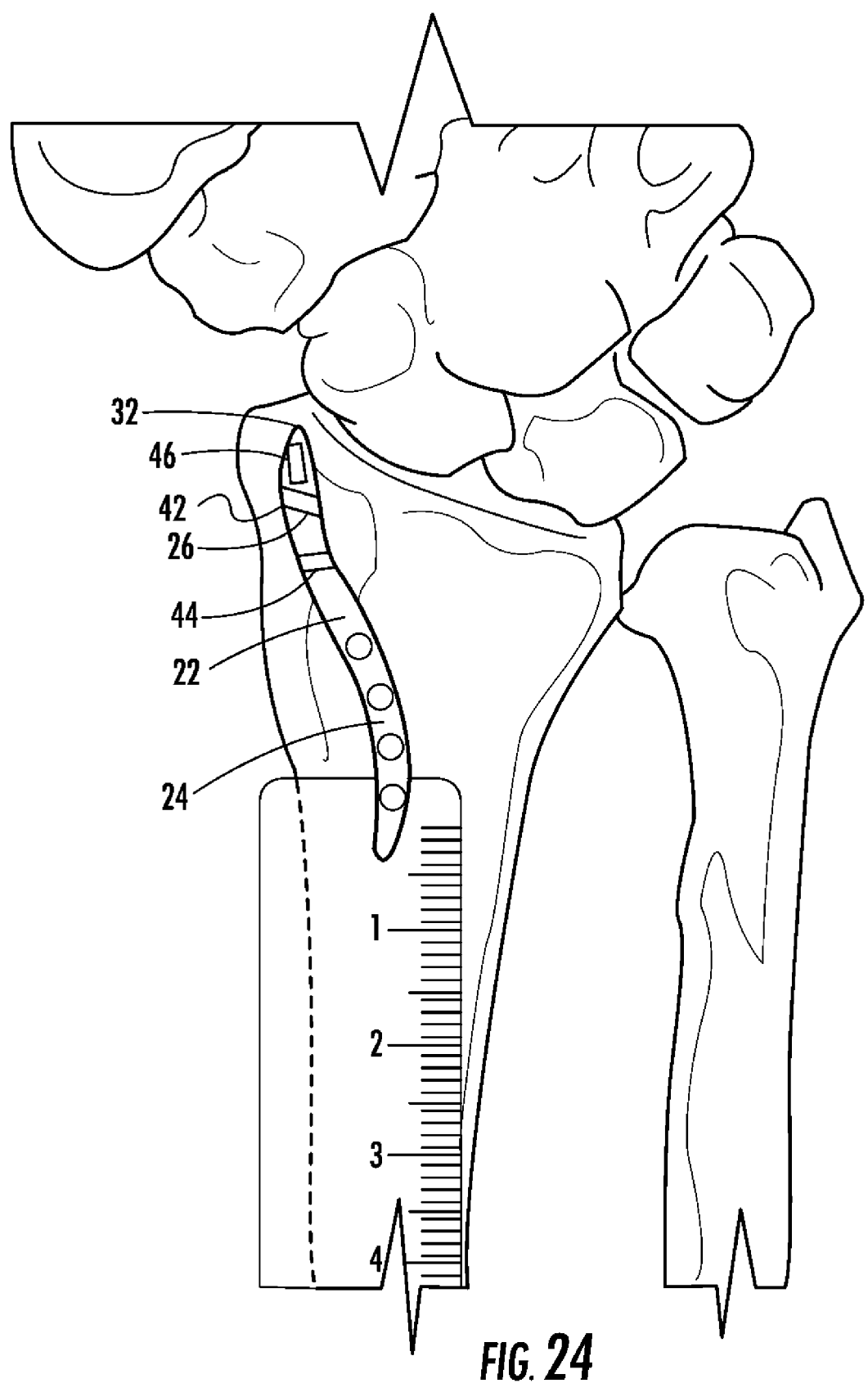
FIG. 24 is a schematic view of an x-ray showing the intramedullary fixation device of the present invention inserted within an intramedullary canal.

As is shown in FIGS. 14 and 23, the drill guide is removed and the cross-locking fasteners 78, 80 are secured in place. Although in FIGS. 14 and 23, the cross-locking fasteners 78, 80 are shown to extend through the implant and across the intramedullary space 52*b* of the second fragment 16, this configuration is for exemplary purposes only. Depending on the nature of the fracture and preference of the medical professional using the implant 22, fasteners that only extend into the second end 26 of the implant 22, such as pegs, rivets, and/or shorter bone screws, can be utilized. The axial driver is removed from the longitudinal receptor 46 either before or after placement of the cross-locking screws, and replaced by the longitudinal fastener 49, e.g. radial styloid bone screw, when fixing a distal radius fracture. This locks the tip 32 of the implant 22 into abutment with the subchondral bone under the radial styloid 20 and secures the second end 26 of the implant 22 to the end portion 18 of the second fragment 16. With firm fixation of the implant 22 in the second fragment 16, the fracture is brought out to length and reduced.

Once the position of the fracture reduction is confirmed, the fracture reduction is secured by insertion of fasteners 84, 86, 88, 90 through the bone 10, and into engagement with the receptors 34, 36, 38, 40 in the first end 24. Depending on the type of fasteners used, the fasteners 84, 86, 88, 90 may extend through the receptors 34, 36, 38, 40 and into the surrounding bone of the first fragment 14. Alternatively, receptors 34, 36, 38, 40 may be threaded and allow the use of unicortical locking screws. Fixation of the implant 22 to the first fragment 14 results in the support of the second fragment 16, in a manner similar to a tent pole supporting a tent; this prevents collapse of the second fragment 16, with resultant loss of length of the bone 10.

Although shown with two cross-locking receptors 42, 44 in the second end 26, any number of fixation members placed in the second end may be applicable depending on the site of application and the size of the implant. In addition, the fixation members may be torsionally disposed to one another to allow more spread to the fixation of the second fragment. In a preferred embodiment, the first receptor 42 is angled to purchase the volar rim of the second fragment 16, placing its entry site dorsally and avoiding contact with the first dorsal compartment tendons; the second receptor 44 is angled distally and dorsally to engage the dorsal ulnar corner of the second fragment 16. In addition, although four fasteners are shown to secure the implant 22 to the first fragment 14, any number of fasteners could be used and would not depart from the spirit and scope of the invention.

The implant may be removed once the fracture site has healed by using a hollow drill bit to core out a section of the radial styloid to enable extraction through the hole. Because the fracture site will have healed over, the implant cannot usually be extracted through the entry site.

FIGS. 25-28 show a third preferred embodiment of the present invention, where the implant 22 comprises a first and second portion 92, 94 that secured together to form a single unit. Once secured together, the first portion 92 comprises the first end 24 of the implant 22 and the second portion 94 comprises the second end 26 of the implant. The first portion 92 has a concave, bent curvature with at least a first receptor 96 for receiving a fastener.

Figure 25:
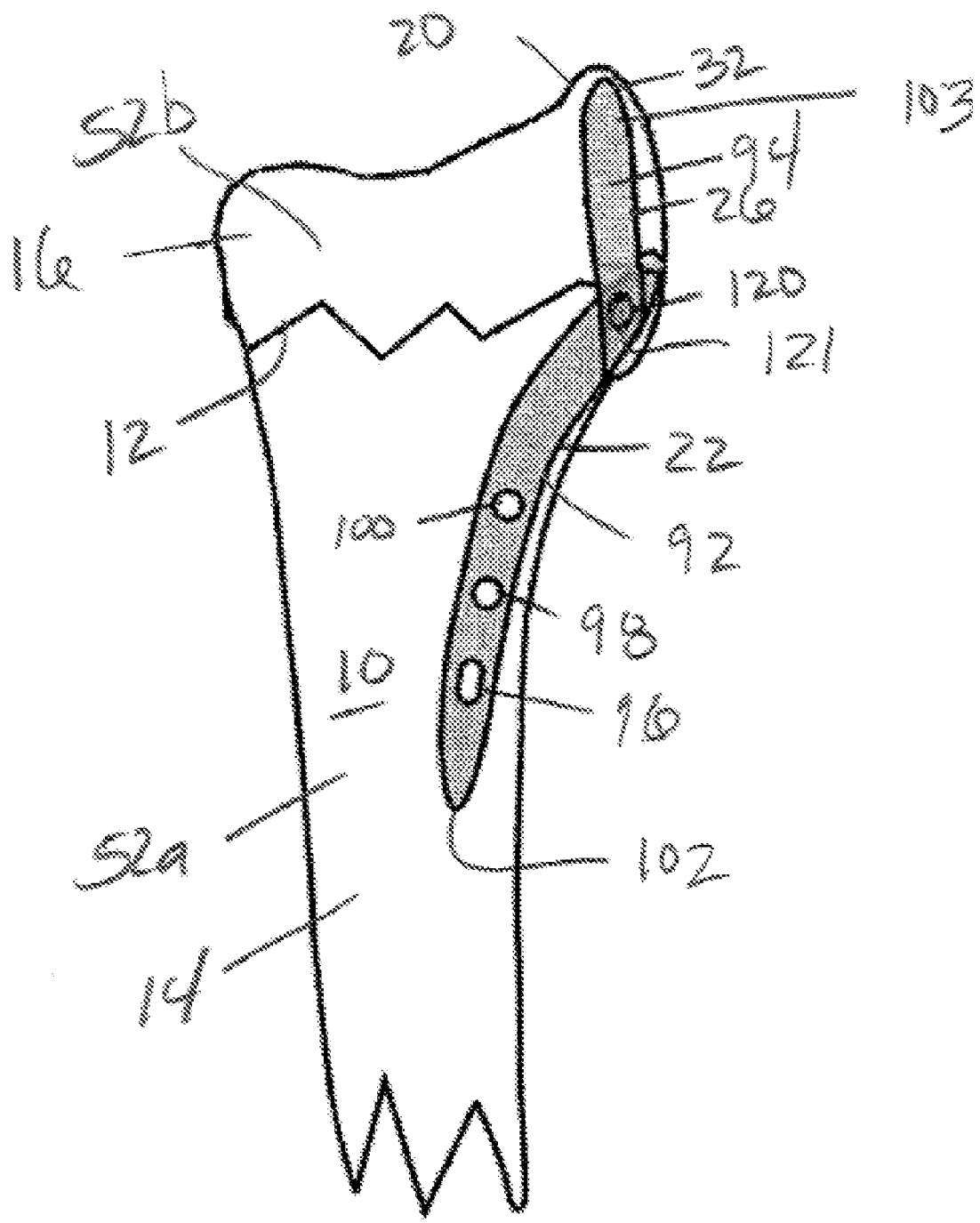
FIGS. 25-28 are elevation views of a second preferred embodiment of the present invention.
Figure 26:
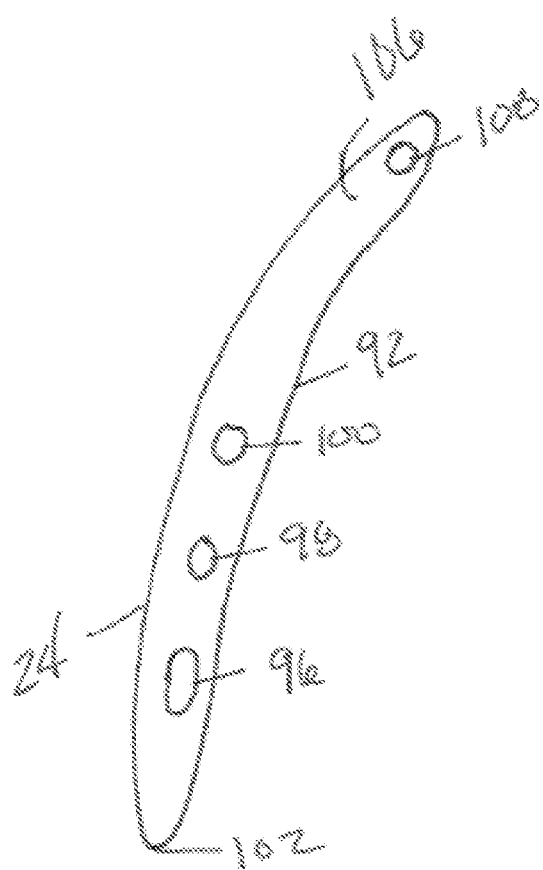
Figure 27:
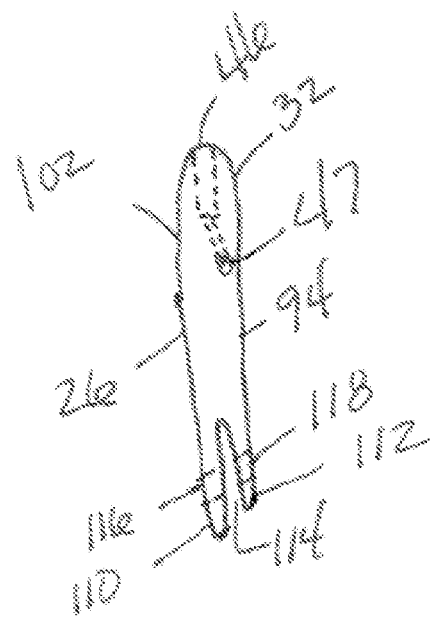
Figure 28:
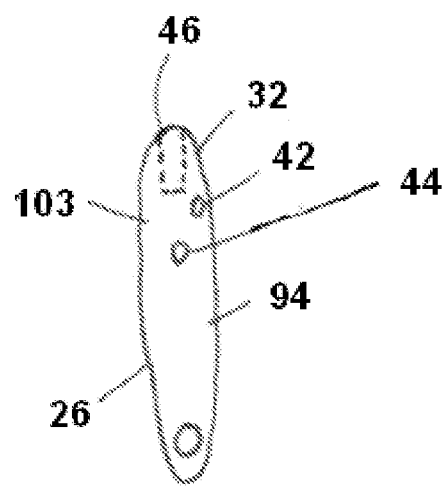

In the embodiment shown in FIG. 25-28 the first end 24 comprises a plurality of receptors 96, 98, 100. The first receptor 96 comprises a slotted aperture enabling fixation of the first end 24 of the implant 22 with a fastener, but also enabling proximal or distal fine-tuning of the fracture reduction when the fastener is only loosely placed within the receptor 96. The second and third 98, 100 receptors consist of screw holes comprising an open-ended channel extending through the width of the implant 22. As is seen in FIG. 25, the plurality of receptors 96, 98, 100 are linearly aligned. However, the receptors 96, 98, 100 may also be radially disposed around the perimeter of the first end 24 to facilitate a cross-locking arrangement. The head 102 of the first end 24 is configured to be the leading edge or drive surface of the first end 24 as it enters the bone through the extended portion 48 of the fracture site 12 (FIG. 1) and is positioned within the intramedullary space 52*a*.

The second end 26 of the implant 22 comprises a support peg 103 configured to abut and support the endosteal surface of the radial styloid portion 20 of the bone 10. As was described with the second end of the implant of the first and second embodiments, the support peg 103 has a substantially round cross-section and a tip 32 having the same general shape and contour of the endosteal surface of the cortical bone at the radial styloid 20. The tip 32 has a generally cone-like shape with a flattened or rounded end. This provides excellent support and strength to the second fragment 16 to resist loss of length of the bone 10 during the healing of the fracture 12.

The tip 32 of the support peg 103 comprises the leading edge or drive surface of the second end 26 when the second end 26 is inserted through the entry point 48, which in this figure comprises the extended portion of the fracture site 12 (FIG. 1) and into the intramedullary space 52*b* of the second fragment 16, as well as serving the load bearing function described above. The second end 26 also comprises an interface for engaging the first end 24 of the implant 22 to form a unitary component.

In the embodiment of the present invention shown in FIGS. 25-28, the interface between the first and second ends 24, 26 of the implant 22 is a tongue and groove assembly. The first end 24 comprises a flattened, tongue portion 106 with a bore 108 extending there through. The second end 26 comprises a first and second arm 110, 112 equidistantly spaced apart across their lengths to form a channel 114 configured to receive the tongue portion 106 of the first end 24. Each arm 110, 112 comprises a concentrically aligned bore 116, 118 for receiving a fastener.

When the tongue portion 106 engages the channel 114, the bores 108, 116, 118 align to form a through hole 120 for receiving a fastener 121 to secure the first and second ends 24, 26 together. In one embodiment, the bores 108, 116, and 118 are threaded and configured to receive a threaded fastener such as a screw. A peg or rivet may also be used to secure the first and second ends 24, 26. In addition, the bores 116, 118 may be slotted to provide for additional distal or proximal fine tuning of the placement of the implant 22 when a fastener 121 is loosely placed within the through hole 120. Other connections are also possible, such as a conical trunion that mates with a morse taper assembly (not shown) as is commonly known and used with modular prosthetic implants, or a captured channel or slot as is commonly known and used with sliding compression hip screws.

The second end 26 may also comprise a longitudinal receptor 46 at the tip 32 for receiving and capturing a fastener configured to mate the implant to the strong cortical bone in radial styloid 20 of the distal fragment 16. In one embodiment of the present invention, the longitudinal receptor 46 comprises a threaded screw hole comprising an aperture and threaded channel bored into the tip 32. In the preferred embodiment of the present invention, the longitudinal fastener is a radial styloid bone screw, such as the radial styloid bone screw 49 shown in FIG. 14. However, other suitable fasteners may also be used, such as pegs or rivets. The diameter of the second end 26 of the implant is significantly larger than the diameter of the longitudinal receptor 46 in order to allow the implant to support axial loading during fracture reduction and fixation. After placement of the implant within the intramedullary space 52b and abutment of the tip 32 against the endosteal surface of the cortical bone of the radial styloid 20, the radial styloid screw is used to hold the implant in position against the cortical bone.

The tip 32 may also comprise a cannulated channel 47 that extends from the tip 32 through a segment of the second end 26 of the implant 10. The channel 47 is configured to receive and enable passage of a guide wire extending from the radial styloid of the second fragment to guide the implant 22 into proper position. In a preferred embodiment of the present invention, the cannulated channel 47 is integrally formed and coaxially aligned with the longitudinal receptor 46. However, the cannulated channel 47 may also be formed independent of the longitudinal receptor 46.

In this embodiment of the present invention, the second end 26 may also comprise a first and second cross-locking receptor 42, 44 for receiving and capturing a fastener. Each receptor 42, 44 comprises a screw hole having an open-ended channel extending diametrically through the second end of the implant 22. The first and second cross-locking receptors 42, 44 are radially spaced apart from each other. This arrangement enables engagement of the volar subchondral bone of the second fragment 16 by a fastener that is captured by and extending through the first receptor 42 and engagement of the dorsal subchondral bone of the second fragment 16 by a fastener that is captured by and extends through the second receptor 44.

In operation, the implant 22 according to the third preferred embodiment of the present invention is inserted within the intramedullary space of the bone in a similar manner to methodology described with respect to the first and second embodiments, with the added step of placing and inserting the first and second ends 24, 26 of the implant 22 into the intramedullary space of the bone 52 in two separate steps and then securing the components together to form a unitary structure. In a first step, the first end is 24 is inserted through the entry site 48 into the intramedullary space 52a of the first fragment 14. A fastener is placed loosely from dorsal to volar in the first, slotted receptor 96 in the first end 24 to fix the first end 24 to the first fragment 14, but still enabling fine-tuning of the implant, and consequently the fracture reduction.

In the next step, the second end 26 is inserted through the entry point 48 and into the intramedullary space 52b of the second fragment 16. Once the second end 26 is properly positioned with respect to the endosteal surface of the radial styloid and the bores 116, 118 of the second end 26 are aligned with the bore 108 of the first end 24 to form the through hole 120, a fastener 122 is inserted within the through hole 120 and loosely placed to enable additional fine tuning of the fracture reduction. Fasteners are then placed within the receptors in the second end 26 to secure the second end 26 to the second fragment 16. Once the fracture has been properly reduced, the fastener loosely placed in the first receptor 96 is tightened and additional fasteners may be placed within the second and third receptors 98, 100, to securely fasten the first end 24 to the first fragment 14.

In the preferred embodiments of the invention described herein, the implant 22 has been positioned within the intramedullary space of the bone by utilizing a plurality of drivers with threaded ends to engage threaded receptors disposed on the implant. FIGS. 29-32 show alternative, yet preferred assemblies and structures for properly positioning the implant of the present invention by advancing the implant across the intramedullary space of the fractured bone.

Figure 29:
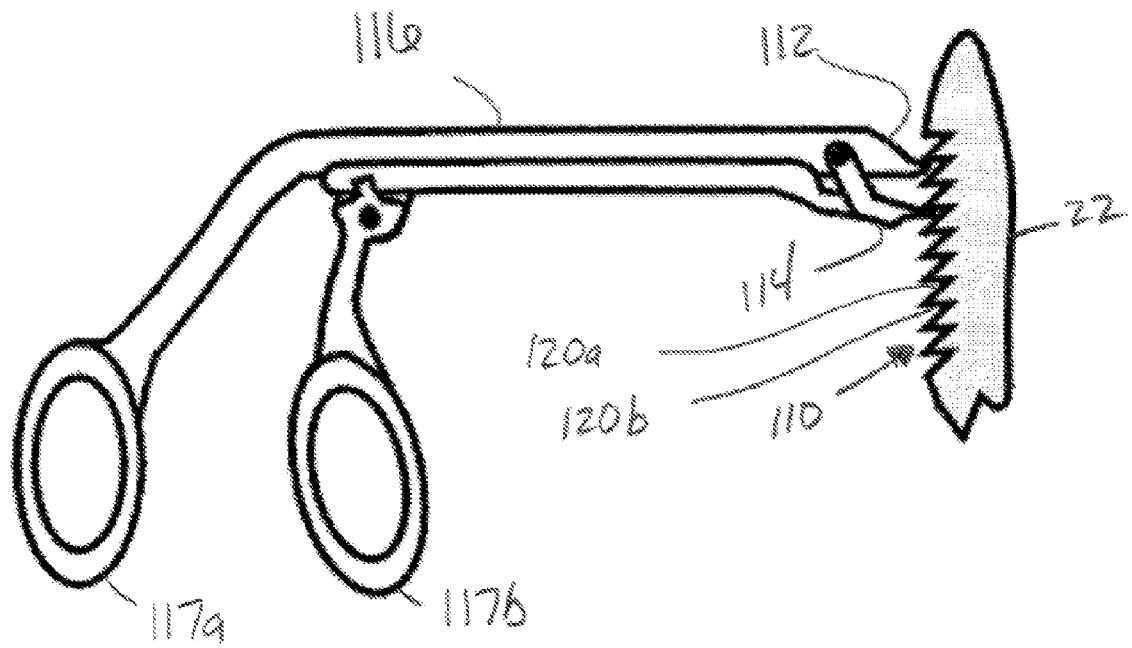
FIGS. 29-32 are elevation views of mechanisms for positioning the implant of the present invention.
Figure 30:
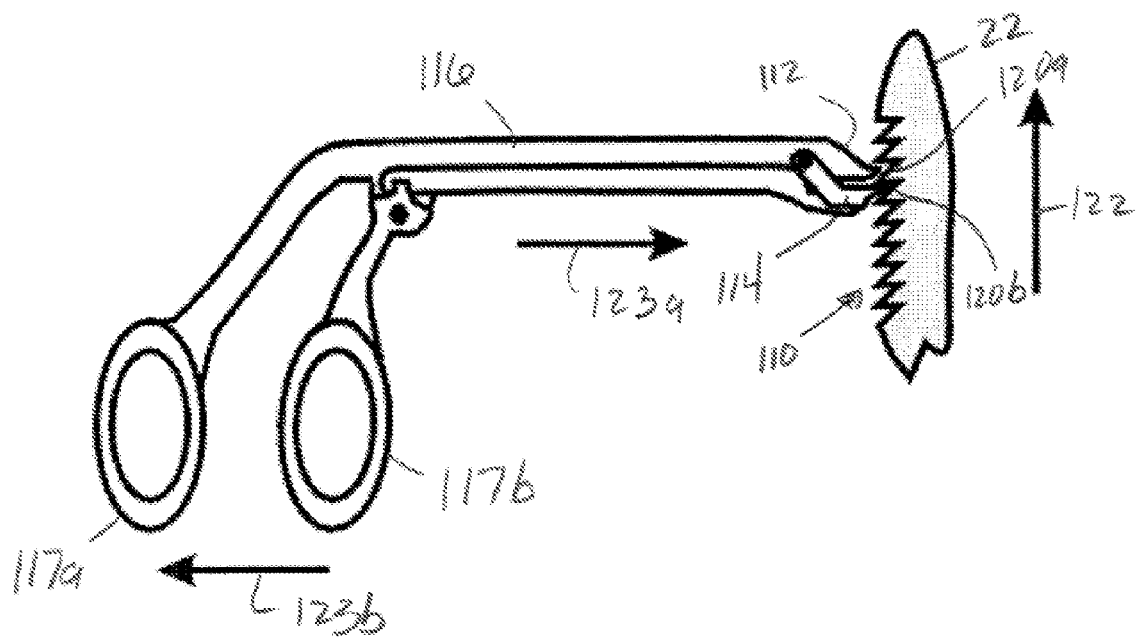

Referring first to FIGS. 29 and 30, the periphery of the implant 22 comprises a serrated surface 110 for engaging the teeth 112, 114 of a ratcheting mechanism 116. The serrated surface 110 comprises a plurality of teeth each having an angled wall 120a orientated upwards towards the tip 32 of the implant 22 and a base wall 120b. In FIG. 21, when the ratcheting mechanism 116 is in the open position, its teeth 112, 114 engage a first and second tooth of the serrated edge 110 where the first and second tooth are separated by an intervening tooth. The ratcheting mechanism 116 closes by drawing handle 117b towards handle 117a along the direction shown by arrow 123b. This causes the teeth 112, 114 to close. As the ratcheting mechanism 116 is closing, the tooth 112 of the ratcheting mechanism 116 will slide off of an angled surface 120a and re-engage the angled surface 120a of the tooth immediately below. Repeating this procedure will gradually displace the implant 22 in the direction of arrow 122.

Figure 31:
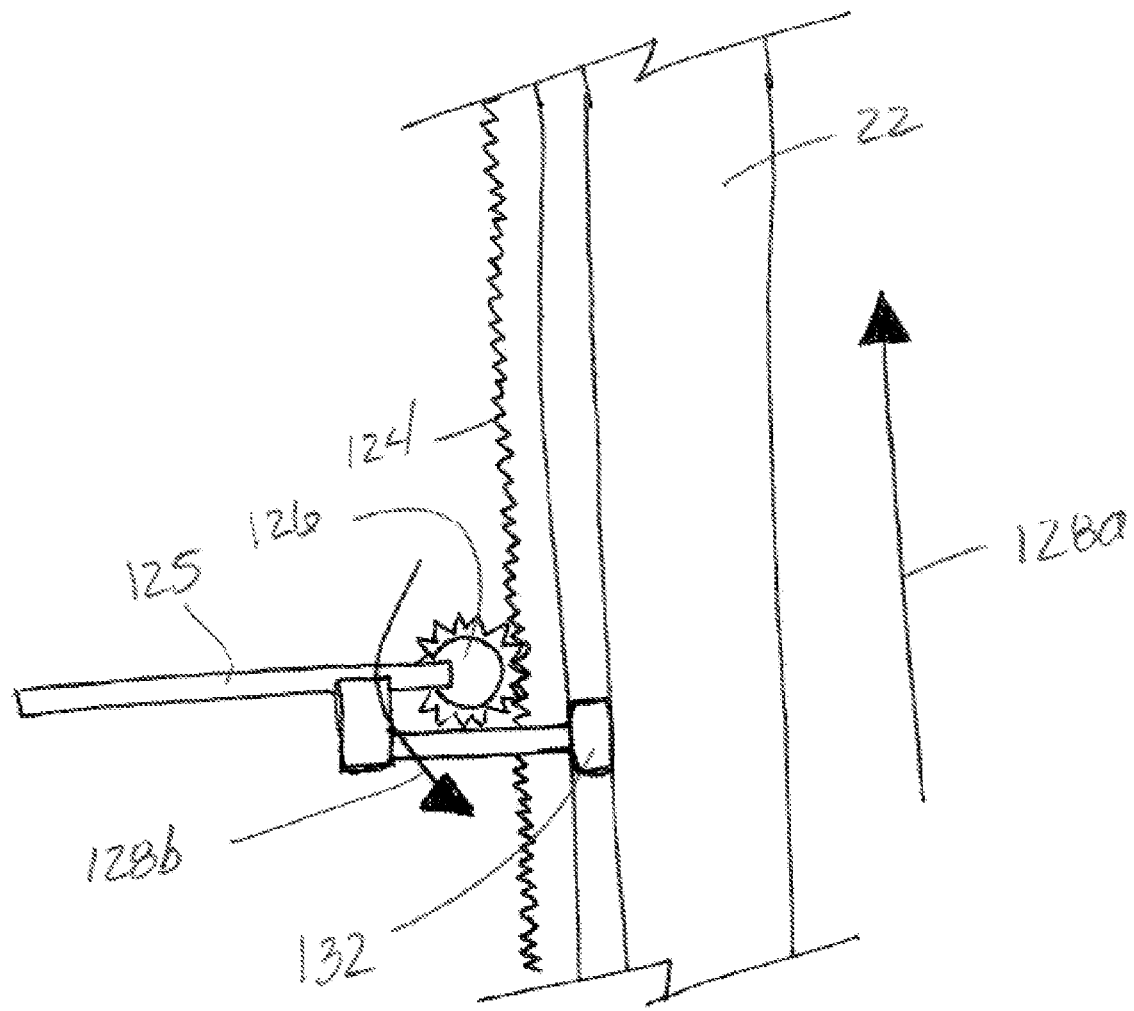

Referring to FIG. 31, the implant 22 comprises a ribbed surface 124. A positioning instrument 125 with a rotating gear 126 is used to advance the implant in the direction of arrow 128a. As the gear 126 rotates in the direction of arrow 128b, the implant is advanced. The implant 22 also includes at least a first channel 130 extending in a parallel direction to the ribbed surface 124. The channel 130 is configured to receive a guide 132 on the positioning instrument 125 that aids in keeping the positioning instrument 125 in engagement with the implant 22.

Figure 32:
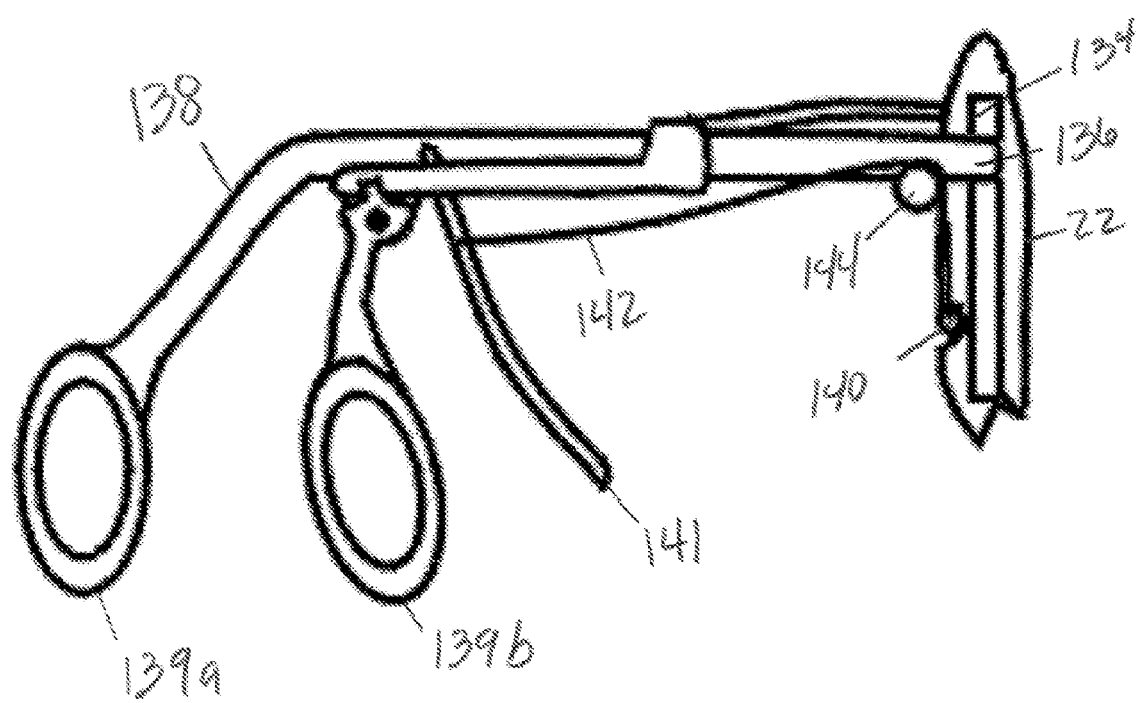

FIG. 32 shows an assembly wherein the implant 22 comprises at a first track disposed longitudinally on the implant. In this embodiment, a first 134 and second (not shown) track on opposing sides of the implant 22 are utilized. Alternatively, this may be a single track with a tongue in groove surface (not shown). The tracks are configured to receive at least a first tongue member 136 of a positioning instrument 138. Closing the positioning instrument by drawing handle 139b towards handle 139a causes the tongue member 136 to engage the track 134 and hold the implant 22. A hole or slot 140 is disposed on the surface of the implant and is configured to receive a suture or flexible wire or ribbon 142 associated with positioning instrument 138. The suture or wire 142 overlies a pulley 144 and is attached to a lever 141. When the lever 141 is moved from a first position to a second position, the suture or wire 142 is pulled and displaces the implant 22 across the fracture site 12 into position in the second fragment 16.

It will be understood that modifications and variations may be effected without departing from the spirit and scope of the present invention. It will be appreciated that the present disclosure is intended as an exemplification of the invention and is not intended to limit the invention to the specific embodiments illustrated and described. The disclosure is intended to cover, by the appended claims, all such modifications as fall within the scope of the claims.

I claim:

1. A method of fracture fixation for fixation of a broken bone comprising a fracture site, a first fragment and a second fragment on opposing sides of the fracture site, and an intramedullary space within the bone, with portions of the intramedullary space on opposing sides of the fracture site, the method comprising:
    obtaining an implant having a first end and a second end;
    inserting at least a portion of the implant in a first direction into the intramedullary space of the first fragment through an entry point on the bone;
    displacing at least a portion of the implant across the fracture site in a second, substantially opposite direction to position the second end of the implant in the intramedullary space of the second fragment;
    affixing the second end to the second fragment; and
    affixing the first end to the first fragment;
    wherein the step of displacing at least a portion of the implant across the fracture site comprises the sub-steps of:
    forming an aperture in the second fragment;
    inserting at least a portion of a positioning instrument through the aperture;
    coupling at least a portion of the positioning instrument to at least a portion of the implant; and
    pulling at least a portion of the positioning instrument back through the aperture to, in turn, displace at least a portion of the implant across the fracture site in a second, substantially opposite direction.

2. The method according to claim 1, further comprising the step of adjusting the angular positioning of the implant within the second fragment.

3. The method according to claim 1, wherein the second fragment comprises an end portion with an endosteal surface having a contour.

4. The method according to claim 3, wherein the second end of the implant has a tip comprising a contour substantially corresponding to the contour of the endosteal surface, and wherein the step of displacing further comprises displacing the implant across the fracture site and into the intramedullary space of the second fragment until the tip abuts the endosteal surface.

5. The method according to claim 1, further comprising the step of forming a pathway in the intramedullary space of the second fragment to receive the second end of the implant.

6. The method according to claim 1, further comprising the step of reducing the fracture.

7. A method of fracture fixation for fixation of a broken bone comprising a fracture site, a first fragment and a second fragment on opposing sides of the fracture site, and an intramedullary space within the bone, with portions of the intramedullary space on opposing sides of the fracture site, the method comprising:
    obtaining an implant having a first end, a second end, and an operative surface configured to be engaged by a positioning instrument, wherein the operative surface comprises a serrated surface having a plurality of teeth;
    inserting at least a portion of the implant in a first direction into the intramedullary space of the first fragment through an entry point on the bone;
    engaging the operative surface of the implant with the positioning instrument;
    actuating the positioning instrument; and
    displacing at least a portion of the second end of the implant across the fracture site in a second, substantially opposite direction and into the second fragment.

8. The method according to claim 7 wherein the positioning instrument comprises a ratcheting mechanism having a plurality of teeth configured to engage the teeth of the serrated surface of the implant.

9. The method according to claim 8, wherein the step of actuating the positioning instrument comprises closing the ratcheting mechanism to displace the second end of the implant into the second fragment.

10. A method of fracture fixation for fixation of a broken bone comprising a fracture site, a first fragment and a second fragment on opposing sides of the fracture site, and an intramedullary space within the bone, with portions of the intramedullary space on opposing sides of the fracture site, the method comprising:
    obtaining an implant having a first end, a second end, and a receptor configured to receive a displacement means operatively associated with a positioning instrument for displacing the second end of the implant across the fracture site and into the second fragment;
    inserting at least a portion of the implant in a first direction into the intramedullary space of the first fragment through the fracture site;
    engaging the displacement means with the receptor; and
    displacing at least a portion of the second end of the implant across the fracture site in a second, substantially opposite direction and into the second fragment
    wherein the implant includes at least one track extending longitudinally along at least a portion of a periphery of the implant, the positioning instrument includes at least one tongue configured to engage the at least one track, and actuating the positioning instrument causes the at least one tongue to engage the at least one track.

11. The method according to claim 10, wherein the displacement means is selected from the group comprising flexible wire, ribbon and suture.

12. The method according to claim 10, wherein the displacement means comprises a pin threadably attachable to the receptor.

13. The method according to claim 12, further comprising the step of placing the pin through at least a portion of the second fragment.

14. The method according to claim 10, further comprising the step of actuating the positioning instrument.

* * * * *